United States Patent
Iveson et al.

(10) Patent No.: US 9,259,496 B2
(45) Date of Patent: Feb. 16, 2016

(54) TECHNETIUM LABELLED PEPTIDES

(75) Inventors: Peter Brian Iveson, Amersham (GB); Bard Indrevoll, Oslo (NO); Ben Newton, Amersham (GB); Rajiv Bhalla, Amersham (GB); Edvin Wilhelm Johannesen, Oslo (NO)

(73) Assignee: GE Healthcare Limited, Buckinghamshire (GB)

( * ) Notice: Subject to any disclaimer, the term of this patent is extended or adjusted under 35 U.S.C. 154(b) by 15 days.

(21) Appl. No.: 14/002,021

(22) PCT Filed: Mar. 2, 2012

(86) PCT No.: PCT/EP2012/053614
§ 371 (c)(1),
(2), (4) Date: Aug. 28, 2013

(87) PCT Pub. No.: WO2012/119937
PCT Pub. Date: Sep. 13, 2012

(65) Prior Publication Data
US 2014/0004041 A1    Jan. 2, 2014

Related U.S. Application Data

(60) Provisional application No. 61/449,102, filed on Mar. 4, 2011.

(30) Foreign Application Priority Data

Mar. 4, 2011    (GB) .................................. 1103696.9

(51) Int. Cl.
A61K 51/00    (2006.01)
A61M 36/14    (2006.01)
A61K 51/08    (2006.01)

(52) U.S. Cl.
CPC ............. *A61K 51/08* (2013.01); *A61K 51/088* (2013.01)

(58) Field of Classification Search
CPC ...... A61K 51/00; A61K 51/08; A61K 51/088
USPC .............. 424/1.11, 1.65, 9.1, 9.2; 514/1, 1.1, 514/19.2, 19.3; 534/7, 10–16; 530/300
See application file for complete search history.

(56) References Cited

U.S. PATENT DOCUMENTS

| | | | | |
|---|---|---|---|---|
| 7,597,875 B2 * | 10/2009 | Archer et al. | ................ | 424/1.65 |
| 8,044,175 B2 * | 10/2011 | Dransfield et al. | ............ | 530/326 |
| 8,431,111 B2 * | 4/2013 | Nairne et al. | .................. | 424/9.6 |
| 8,529,874 B2 * | 9/2013 | Johannesen et al. | ........... | 424/9.6 |
| 8,568,693 B2 * | 10/2013 | Danikas et al. | ................ | 424/9.2 |
| 2009/0274623 A1 | 11/2009 | Smith et al. | | |

FOREIGN PATENT DOCUMENTS

| | | |
|---|---|---|
| EP | 1952826 | 8/2008 |
| WO | 02/070018 | 9/2002 |
| WO | 03/006070 | 1/2003 |
| WO | 03/057155 | 7/2003 |
| WO | 2004/062568 | 7/2004 |
| WO | 2004/078778 | 9/2004 |
| WO | 2008/139207 | 11/2008 |
| WO | 2009016180 | 8/2009 |
| WO | 2009/106566 | 9/2009 |
| WO | 2011/048029 | 4/2011 |
| WO | 2012/022676 | 2/2012 |

OTHER PUBLICATIONS

GB1103696.9 Search Report Dated Aug. 10, 2011.
PCT/EP2012/053614 ISRWO Dated May 16, 2012.

* cited by examiner

*Primary Examiner* — D L Jones
(74) *Attorney, Agent, or Firm* — Parks Wood LLC; Collen A. Beard, Esq.

(57) ABSTRACT

The present invention relates to technetium imaging agents comprising radiolabeled c-Met binding peptides suitable for SPECT or PET imaging in vivo. The c-Met binding peptides are labelled via chelator conjugates. Also disclosed are pharmaceutical compositions, methods of preparation of the agents and compositions, plus methods of in vivo imaging using the compositions, especially for use in the diagnosis of cancer.

13 Claims, No Drawings

TECHNETIUM LABELLED PEPTIDES

This application is a filing under 35 U.S.C. 371 of international application number PCT/EP2012/053614, filed Mar. 2, 2012, which claims priority to Great Britain application number 1103696.9 filed Mar. 4, 2011 and to U.S. application No. 61/449,102 filed Mar. 4, 2011, the entire disclosure of which is hereby incorporated by reference.

FIELD OF THE INVENTION

The present invention relates to technetium imaging agents comprising radiolabelled c-Met binding peptides suitable for SPECT or PET imaging in vivo. The c-Met binding peptides are labelled via chelator conjugates. Also disclosed are pharmaceutical compositions, methods of preparation of the agents and compositions, plus methods of in vivo imaging using the compositions, especially for use in the diagnosis of cancer.

BACKGROUND TO THE INVENTION

Hepatocyte growth factor (HGF), also known as scatter factor (SF), is a growth factor which is involved in various physiological processes, such as wound healing and angiogenesis. The high affinity interaction of HGF interaction with its receptor (c-Met) is implicated in tumour growth, invasion and metastasis.

Knudsen et al have reviewed the role of HGF and c-Met in prostate cancer, with possible implications for imaging and therapy [Adv. Cancer Res., 91, 31-67 (2004)]. Labelled anti-met antibodies for diagnosis and therapy are described in WO 03/057155.

c-Met has been shown to be involved in tumour growth, invasion and metastasis in many human cancers of epithelial origin. c-Met is expressed by most carcinomas and its elevated expression relative to normal tissue has been detected in many cancers, including: lung, breast, colorectal, pancreatic, head and neck, gastric, hepatocellular, ovarian, renal, glioma, melanoma and a number of sarcomas. In colorectal carcinoma (CRC), over-expression of c-Met has been detected in dysplastic aberrant crypt foci, the earliest pre-neoplastic lesions of the disease. In head and neck squamous cell cancer, c-Met is reportedly expressed or overexpressed in roughly 80% of primary tumours. In prostate cancer metastasis to bone, c-Met was reported overexpressed in over 80% of bone metastasis.

Under normal conditions, c-Met is expressed on epithelial cells and activated in a paracrine fashion, by mesenchymally derived HGF. The activation of c-Met in normal cells is a transient event and is tightly regulated. In tumour cells, however, c-Met can be constitutively active. In cancer, aberrant c-Met stimulation can be achieved through c-Met amplification/over-expression, activating c-Met mutations (e.g. structural alterations) and acquisition of autonomous growth control through creation of autocrine signalling loops. In addition, a defective down-regulation of the c-Met receptor will also contribute to aberrant c-Met expression in the cell membrane. While the over-expression of c-Met is HGF dependent (autocrine/paracrine), structural alterations caused by mutations are HGF independent (e.g. loss of extracellular domain).

WO 2004/078778 discloses polypeptides or multimeric peptide constructs which bind c-Met or a complex comprising c-Met and HGF. Approximately 10 different structural classes of peptide are described. WO 2004/078778 discloses that the peptides can be labelled with a detectable label for in vitro and in vivo applications, or with a drug for therapeutic applications. The detectable label can be: an enzyme, a fluorescent compound, an optical dye, a paramagnetic metal ion, an ultrasound contrast agent or a radionuclide. Preferred labels of WO 2004/078778 are stated to be radioactive or paramagnetic, and most preferably comprise a metal which is chelated by a metal chelator. WO 2004/078778 states that the radionuclides therein can be selected from: $^{18}$F, $^{124}$I, $^{125}$I, $^{131}$I, $^{123}$I, $^{77}$Br, $^{76}$Br, $^{99m}$Tc, $^{51}$Cr, $^{67}$Ga, $^{68}$Ga, $^{47}$Sc, $^{167}$Tm, $^{141}$Ce, $^{111}$In, $^{168}$Yb, $^{175}$Yb, $^{140}$La, $^{90}$Y, $^{88}$Y, $^{153}$Sm, $^{166}$Ho, $^{165}$Dy, $^{166}$Dy, $^{62}$Cu, $^{64}$Cu, $^{67}$Cu, $^{97}$Ru, $^{103}$Ru, $^{186}$Re, $^{203}$Pb, $^{211}$Bi, $^{212}$Bi, $^{213}$Bi, $^{214}$Bi, 105Rh, $^{109}$Pd, $^{117m}$Sn, $^{149}$Pm, $^{161}$Tb, $^{177}$Lu, $^{198}$Au and $^{199}$Au. WO 2004/078778 states (page 62) that the preferred radionuclides for diagnostic purposes are: $^{64}$Cu, $^{67}$Ga, $^{68}$Ga, $^{99m}$Tc and $^{111}$In, with $^{99m}$Tc being particularly preferred.

WO 2004/078778 teaches at Examples 14-17 methods of increasing the serum residence time of the c-Met binding peptides: conjugation to a moiety which binds non-covalently to human serum albumin; conjugation to PEG; fusion to serum protein and conjugation to maleimide.

WO 2009/016180 discloses imaging agents which comprises a conjugate of Formula I:

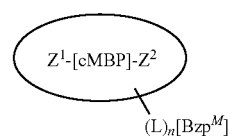

(I)

where:
$Z^1$ is attached to the N-terminus of cMBP, and is H or $M^{IG}$;
$Z^2$ is attached to the C-terminus of cMBP and is OH, $OB^c$, or $M^{IG}$,
  where $B^c$ is a biocompatible cation;
cMBP is a cMet binding cyclic peptide of 17 to 30 amino acids which comprises the amino acid sequence (SEQ-1):
$Cys^a$-$X^1$-$Cys^c$-$X^2$-Gly-Pro-Pro-$X^3$-Phe-Glu-$Cys^d$-Trp-$Cys^b$-Tyr-$X^4$-$X^5$-$X^6$;
wherein $X^1$ is Asn, His or Tyr;
  $X^2$ is Gly, Ser, Thr or Asn;
  $X^3$ is Thr or Arg;
  $X^4$ is Ala, Asp, Glu, Gly or Ser;
  $X^5$ is Ser or Thr;
  $X^6$ is Asp or Glu;
  and $Cys^{a-d}$ are each cysteine residues such that residues a and b as well as c and d are cyclised to form two separate disulfide bonds;
$M^{IG}$ is a metabolism inhibiting group;
L is a synthetic linker group;
$Bzp^M$ is a benzopyrylium dye.

WO 2008/139207 discloses cMet binding cyclic peptide similar to those of WO 2009/016180, in this case labelled with a particular class of cyanine dyes.

The optical imaging agents of WO 2009/016180 and WO 2008/139207 are said to be useful for optical imaging to obtain images of sites of c-Met over-expression or localisation in vivo, particularly for imaging colorectal cancer.

THE PRESENT INVENTION

The present invention relates to imaging agent compositions comprising radioactive technetium ($^{99m}$Tc or $^{94m}$Tc) labelled c-Met binding peptides suitable for positron emission tomography (PET) or single photon emission tomography (SPECT) imaging in vivo. The c-Met binding peptides are labelled via a chelator conjugate of the peptide with a diaminedioxime ligand. The conjugates are radiolabelled with technetium under mild, room temperature conditions giving the desired radiometal complex in high yield and radiochemical purity. The $^{99m}$Tc imaging agents can be readily prepared form a sterile, non-radioactive kit which is reconstituted with [$^{99m}$Tc]-pertechnetate from a commercial $^{99m}$Tc generator.

The imaging agents exhibit good, target-specific tumour uptake in vivo. The imaging agents also appear in addition to be well tolerated in preclinical models.

DETAILED DESCRIPTION OF THE INVENTION

In a first aspect, the present invention provides an imaging agent which comprises a radioactive $^x$Tc complex of a chelator conjugate of a c-Met binding peptide, said chelator conjugate being of Formula I:

$$Z^1\text{-}[cMBP]\text{-}Z^2 \quad (I)$$

where:
$^x$Tc is the radioisotope $^{94m}$Tc or $^{99m}$Tc;
cMBP is an 18 to 30-mer c-Met binding cyclic peptide of Formula II:

$$\text{-}(A)_x\text{-}Q\text{-}(A')_y\text{-} \quad (II)$$

where Q is the amino acid sequence (SEQ-1):
-Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$-
wherein X$^1$ is Asn, His or Tyr;
X$^2$ is Gly, Ser, Thr or Asn;
X$^3$ is Thr or Arg;
X$^4$ is Ala, Asp, Glu, Gly or Ser;
X$^5$ is Ser or Thr;
X$^6$ is Asp or Glu;
and Cys$^{a-d}$ are each cysteine residues such that residues a and b as well as c and d are cyclised to form two separate disulfide bonds;
A and A' are independently any amino acid other than Cys, or one of A and A' is Lys($\epsilon$-Z$^3$);
x and y are independently integers of value 0 to 13, and are chosen such that [x+y]=1 to 13;
Z$^1$ is attached to the N-terminus of cMBP, and is M$^{IG}$ or Z$^3$;
Z$^2$ is attached to the C-terminus of cMBP and is M$^{IG}$ or Z$^3$;
  wherein each M$^{IG}$ is independently a metabolism inhibiting group
  which is a biocompatible group which inhibits or suppresses in vivo metabolism of the cMBP peptide;
Z$^3$ is a chelator of Formula (III):

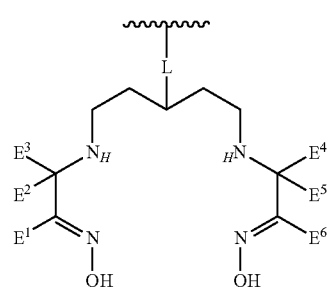

(III)

wherein E$^1$-E$^6$ are each independently an R' group;
each R' is independently H or $C_{1-4}$ alkyl, $C_{3-7}$ alkylaryl, $C_{2-7}$ alkoxyalkyl, $C_{1-4}$ hydroxyalkyl, $C_{1-4}$ fluoroalkyl, $C_{2-7}$ carboxyalkyl or $C_{1-4}$ aminoalkyl, or two or more R' groups together with the atoms to which they are attached form a carbocyclic, heterocyclic, saturated or unsaturated ring;
L is a synthetic linker group of formula -(A)$_m$- wherein each A is independently —CR$_2$—, —CR═CR—, —C≡C—, —CR$_2$CO$_2$—, —CO$_2$CR$_2$—, —NRCO—, —CONR—, —NR(C═O)NR—, —NR(C═S)NR—, —SO$_2$NR—, —NRSO$_2$—, —CR$_2$OCR$_2$—, —CR$_2$SCR$_2$—, —CR$_2$NRCR$_2$—, a $C_{4-8}$ cycloheteroalkylene group, a $C_{4-8}$ cycloalkylene group, a $C_{5-12}$ arylene group, or a $C_{3-12}$ heteroarylene group, or a monodisperse polyethyleneglycol (PEG) building block;
each R is independently chosen from H, $C_{1-4}$ alkyl, $C_{2-4}$ alkenyl, $C_{2-4}$ alkynyl, $C_{1-4}$ alkoxyalkyl or $C_{1-4}$ hydroxyalkyl;
m is an integer of value 1 to 10;
with the proviso that the conjugate of Formula I comprises one Z$^3$ group and said Z$^3$ group forms a metal complex with the $^x$Tc.

By the term "imaging agent" is meant a compound suitable for imaging the mammalian body. Preferably, the mammal is an intact mammalian body in vivo, and is more preferably a human subject. The imaging agent is typically administered in a non-pharmacologic amount, i.e. at a dosage designed to have a minimal biological effect on the mammalian subject. Preferably, the imaging agent can be administered to the mammalian body in a minimally invasive manner, i.e. without a substantial health risk to the mammalian subject when carried out under professional medical expertise. Such minimally invasive administration is preferably intravenous administration into a peripheral vein of said subject, without the need for local or general anaesthetic.

The term "in vivo imaging" as used herein refers to those techniques that non-invasively produce images of all or part of an internal aspect of a mammalian subject.

By the term "chelator conjugate" is meant that chelator is covalently bonded to the cMBP peptide.

By the term "c-Met binding cyclic peptide" is meant a peptide which binds to the hepatocyte growth factor receptor, also known as c-Met (or simply MET). Suitable such peptides of the present invention are cyclic peptides of 18 to 30 amino acids of Formula I. Such peptides have an apparent K$_d$ for c-Met of less than about 20 nM. The cMBP sequence of said peptides comprises proline residues, and it is known that such residues can exhibit cis/trans isomerisation of the backbone amide bond. The cMBP peptides of the present invention include any such isomers. The cMBP of the present invention is suitably used as a monomer, i.e. dimers and/or heterodimers of the cMBP are outside the scope.

The Z$^1$ group substitutes the amine group of the last amino acid residue of the cMBP, i.e., the amino- or N-terminus. The Z$^2$ group substitutes the carbonyl group of the last amino acid residue of the cMBP—i.e. the carboxy or C-terminus.

By the term "metabolism inhibiting group" (M$^{IG}$) is meant a biocompatible group which inhibits or suppresses in vivo metabolism of the cMBP peptide at either the amino terminus (Z$^1$) or carboxy terminus (Z$^2$). For the imaging agents of the present invention, the M$^{IG}$ includes the Z$^3$ group—i.e. the chelator of Formula III. In that case, the technetium complex is covalently attached at the cMBP N- or C-terminus (as Z$^1$ or Z$^2$ respectively), and the technetium complex serves to block metabolism of the cMBP. Other such M$^{IG}$ groups are well known to those skilled in the art and are suitably chosen from, for the peptide amine terminus:

N-acylated groups —NH(C=O)$R^G$ where the acyl group —(C=O)$R^G$ has $R^G$ chosen from: $C_{1-6}$ alkyl, or $C_{3-10}$ aryl groups or comprises a polyethyleneglycol (PEG) building block. Preferred such PEG groups are the biomodifiers of Formula IA or IB:

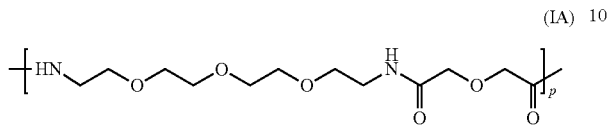

17-amino-5-oxo-6-aza-3,9,12,15-tetraoxaheptadecanoic acid of Formula IA wherein p is an integer from 1 to 10. Alternatively, a PEG-like structure based on a propionic acid derivative of Formula IB can be used:

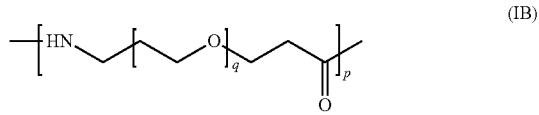

where p is as defined for Formula IA and
q is an integer from 3 to 15.

In Formula IB, p is preferably 1 or 2, and q is preferably 5 to 12.

Preferred such amino terminus $M^{IG}$ groups are acetyl, benzyloxycarbonyl or trifluoroacetyl, most preferably acetyl.

By the term "amino acid" is meant an L- or D-amino acid, amino acid analogue (eg. naphthylalanine) or amino acid mimetic which may be naturally occurring or of purely synthetic origin, and may be optically pure, i.e. a single enantiomer and hence chiral, or a mixture of enantiomers. Conventional 3-letter or single letter abbreviations for amino acids are used herein. Preferably the amino acids of the present invention are optically pure. By the term "amino acid mimetic" is meant synthetic analogues of naturally occurring amino acids which are isosteres, i.e. have been designed to mimic the steric and electronic structure of the natural compound. Such isostere amino acids are known to be used within peptides, and include but are not limited to depsipeptides, retro-inverso peptides, thioamides, cycloalkanes or 1,5-disubstituted tetrazoles [see M. Goodman, Biopolymers, 24, 137, (1985)].

By the term "peptide" is meant a compound comprising two or more amino acids, as defined above, linked by a peptide bond (i.e. an amide bond linking the amine of one amino acid to the carboxyl of another).

When A and A' are "any amino acid other than Cys" that means that the additional amino acids of the A and A' groups lack free thiol groups, in particular Cys residues. That is because an additional Cys residue would risk disulfide bridge scrambling with the $Cys^a$-$Cys^b$ and $Cys^c$-$Cys^d$ disulfide bridges of the Q sequence, with consequent loss of c-Met binding affinity.

In Formula (I), the $Z^3$ group (i.e. the chelator of Formula III) is suitably attached at one of the following locations (i)-(iii):

(i) amino terminus of cMBP, as a $Z^1$ group. Such conjugation would use a carboxy-functionalised chelator of Formula III;

(ii) carboxy terminus of cMBP, as a $Z^2$ group. Such attachment at the C-terminus directly can be achieved using an amine-functionalised chelator of Formula III. For such conjugation, an additional Lys residue to permit chelator conjugation is therefore unnecessary. In addition, the attached technetium complex can function as a $M^{IG}$ group;

(iii) attachment to a Lys (epsilon) amine side chain of a Lys residue located in the A or A' groups.

When x is 94m, the technetium radioisotope is $^{94m}$Tc, which is particularly suitable for positron emission tomography (PET) imaging in vivo. When x is 99m, the technetium radioisotope is $^{99m}$Tc, which is particularly suitable for single photon emission tomography (SPECT) imaging in vivo. Preferably, $^x$Tc is $^{99m}$Tc.

By the term "radioactive $^x$Tc complex of a chelator" is meant a radiometal complex of a chelating agent. By the term "radiometal complex" is meant a coordination metal complex of the radiometal with the chelator of Formula (III), wherein said chelator is covalently bonded to the cMBP peptide via the linker group (L) of Formula I. The term "chelator" or "chelating agent" has its conventional meaning and refers to 2 or more metal donor atoms arranged such that chelate rings result upon metal coordination. The chelator of Formula (III) has a diaminedioxime donor set. Thus, the $^x$Tc complex of the present invention is believed to be of Formula (IV):

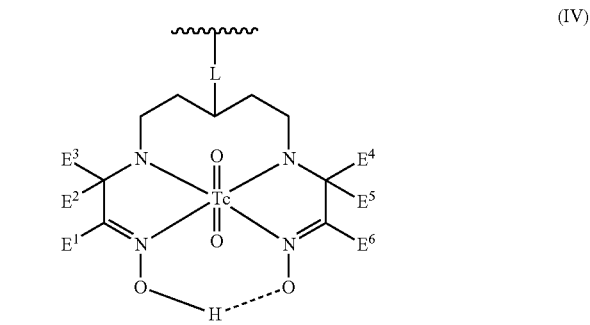

where $E^1$ to $E^6$ and L are as defined for Formula (III).

The terms "comprising" or "comprises" have their conventional meaning throughout this application and imply that the components listed must be present, but that other, unspecified compounds or species may be present in addition. The term 'comprising' includes as a preferred subset "consisting essentially of" which means that the composition has the components listed without other compounds or species being present.

Preferred Features.

Preferred cMBP peptides of the present invention have a $K_d$ for binding of c-Met to c-Met/HGF complex of less than about 10 nM (based on fluorescence polarisation assay measurements), most preferably in the range 1 to 5 nM, with less than 3 nM being the ideal.

The imaging agents of the first aspect are preferably provided in a form suitable for mammalian administration. By the phrase "in a form suitable for mammalian administration" is meant a composition which is sterile, pyrogen-free, lacks compounds which produce toxic or adverse effects, and is formulated at a biocompatible pH (approximately pH 6.5 to 8.5) and physiologically compatible osmolality. Such compositions lack particulates which could risk causing emboli in vivo, and are formulated so that precipitation does not occur on contact with biological fluids (eg. blood). Such compositions also contain only biologically compatible excipients, and are preferably isotonic. A preferred such form is the radiopharmaceutical composition of the fourth aspect (see below).

The imaging agents of the present invention suitably have both cMBP peptide termini protected by $M^{IG}$ groups, which will usually be different. Having both peptide termini protected in this way is important for in vivo imaging applications, since otherwise rapid peptide metabolism would be expected with consequent loss of selective binding affinity for c-Met. When both $Z^1$ and $Z^2$ are $M^{IG}$, preferably $Z^1$ is acetyl and $Z^2$ is a primary amide. Most preferably, $Z^1$ is acetyl and $Z^2$ is a primary amide and the $^xTc$ moiety is attached to the epsilon amine side chain of a lysine residue of cMBP.

Q preferably comprises the amino acid sequence of either SEQ-2 or SEQ-3:

(SEQ-2)
Ser-Cys$^a$-X$^1$-Cys$^c$-X$^2$-Gly-Pro-Pro-X$^3$-Phe-Glu-Cys$^d$-

Trp-Cys$^b$-Tyr-X$^4$-X$^5$-X$^6$;

(SEQ-3)
Ala-Gly-Ser-Cys$^a$-X$^1$-Cys$^c$-X$^2$-Gly-Pro-Pro-X$^3$-Phe-

Glu-Cys$^d$-Trp-Cys$^b$-Tyr-X$^4$-X$^5$-X$^6$-Gly-Thr.

In SEQ-1, SEQ-2 and SEQ-3, $X^3$ is preferably Arg. The cMBP peptide of the first aspect preferably has the amino acid sequence (SEQ-7):

Ala-Gly-Ser-Cys$^a$-Tyr-Cys$^c$-Ser-Gly-Pro-Pro-Arg-Phe-

Glu-Cys$^d$-Trp-Cys$^b$-Tyr-Glu-Thr-Glu-Gly-Thr-Gly-Gly-

Gly-Lys.

The imaging agent of Formula (I) is preferably chosen such that one of A and A' is Lys(ε-$Z^3$) and cMBP comprises only one such Lys residue. More preferably, the single Lys(ε-$Z^3$) moiety is at the carboxy terminus, so that the cMBP is of Formula IIA:

-(A)$_x$-Q-(A')$_z$-Lys(ε-$Z^3$)— (IIA)

wherein:

z is an integer of value 0 to 12, and [x+z]=0 to 12.

In Formula I and Formula II, the -(A)$_x$- or -(A')$_y$- groups preferably comprise a linker peptide which is chosen from:

(SEQ-4)
Gly-Gly-Gly-Lys-, (SEQ-5)
Gly-Ser-Gly-Lys-
or (SEQ-6)
Gly-Ser-Gly-Ser-Lys-, and the $Z^3$ group is attached to the epsilon amine group of the Lys residue of said linker peptide.

The chelator of Formula (III) is preferably attached at either the C-terminus ($Z^2$ group), or as a Lys(ε-$Z^3$) moiety. More preferably it is attached as a Lys(ε-$Z^3$) moiety, and most preferably when the Lys(ε-$Z^3$) moiety is at the carboxy terminus as for Formula (IIA) above.

In the imaging agent of Formula (I), the chelator is preferably of Formula IIIA:

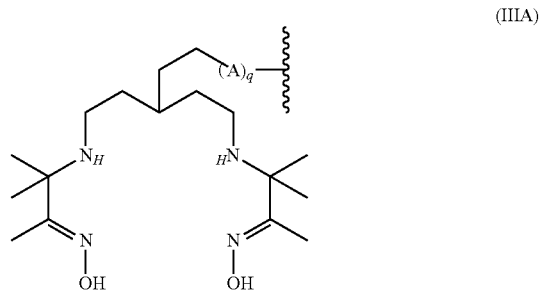

(IIIA)

where q is an integer of value 1 to 6, and A is as defined for Formula (III).

In Formula (IIIA), (A)$_q$ is preferably —(NH)(A)$_t$- where t is an integer of value 0 to 5.

The imaging agents of the first aspect can be prepared as described in the third aspect (below).

In a second aspect, the present invention provides a chelator conjugate of Formula I, as defined in the first aspect. Preferred aspects of the cMBP peptide of Formula (II) and chelator of Formula (III) in the second aspect are as described in the first aspect (above).

The chelator conjugates of the second aspect can be obtained by the bifunctional chelate approach. The term "bifunctional chelate" has its conventional meaning, and refers to a chelating agent having covalently attached thereto a pendant functional group. The functional group is used as a reactive site to attach the chelator to the cMBP peptide. The bifunctional chelate approach and associated syntheses have been described by Bartholoma et al [Chem. Rev., 110(5), 2903-2920 (2010)]; Chakraborty et al [Curr. Top. Med. Chem., 10(11), 1113-1134 (2010)] and Brechbiel et al [Quart. J. Nucl. Med. Mol. Imaging, 52(2), 166-173 (2008)]. The functional group of the present invention is preferably an amine, carboxylic acid or activated ester, more preferably a primary amine or an activated ester. Bifunctional chelators having a pendant amine functional group can be conjugated to the carboxyl group of a peptide. Bifunctional chelators having a carboxyl or activated ester functional group can be conjugated to an amine group of a peptide.

By the term "activated ester" or "active ester" is meant an ester derivative of the associated carboxylic acid which is designed to be a better leaving group, and hence permit more facile reaction with nucleophile, such as amines. Examples of suitable active esters are: N-hydroxysuccinimide (NETS); sulfo-succinimidyl ester; pentafluorophenol; pentafluorothiophenol; para-nitrophenol; hydroxybenzotriazole and PyBOP (i.e. benzotriazol-1-yl-oxytripyrrolidinophosphonium hexafluorophosphate). Preferred active esters are N-hydroxysuccinimide or pentafluorophenol esters, especially N-hydroxysuccinimide esters.

c-Met binding peptides of formula cMBP of the present invention may be obtained by a method of preparation which comprises:

(i) solid phase peptide synthesis of a linear peptide which has the same peptide sequence as the desired cMBP peptide and in which the Cys$^a$ and Cys$^b$ are unprotected, and the Cys$^c$ and Cys$^d$ residues have thiol-protecting groups;

(ii) treatment of the peptide from step (i) with aqueous base in solution to give a monocyclic peptide with a first disulphide bond linking Cys$^a$ and Cys$^b$;

(iii) removal of the Cys$^c$ and Cys$^d$ thiol-protecting groups and cyclisation to give a second disulphide bond linking Cys$^c$ and Cys$^d$, which is the desired bicyclic peptide product Z$^1$-[cMBP]-Z$^2$.

By the term "protecting group" is meant a group which inhibits or suppresses undesirable chemical reactions, but which is designed to be sufficiently reactive that it may be cleaved from the functional group in question under mild enough conditions that do not modify the rest of the molecule. After deprotection the desired product is obtained. Amine protecting groups are well known to those skilled in the art and are suitably chosen from: Boc (where Boc is tert-butyloxycarbonyl), Fmoc (where Fmoc is fluorenylmethoxycarbonyl), trifluoroacetyl, allyloxycarbonyl, Dde [i.e. 1-(4,4-dimethyl-2,6-dioxocyclohexylidene)ethyl] or Npys (i.e. 3-nitro-2-pyridine sulfenyl). Suitable thiol protecting groups are Trt (Trityl), Acm (acetamidomethyl), t-Bu (tert-butyl), tert-Butylthio, methoxybenzyl, methylbenzyl or Npys (3-nitro-2-pyridine sulfenyl). The use of further protecting groups are described in *Protective Groups in Organic Synthesis, 4$^{th}$ Edition*, Theorodora W. Greene and Peter G. M. Wuts, [Wiley Blackwell, (2006)]. Preferred amine protecting groups are Boc and Fmoc, most preferably Boc. Preferred thiol protecting groups are Trt and Acm.

Examples 1 and 2 provide further specific details. Further details of solid phase peptide synthesis are described in P. Lloyd-Williams, F. Albericio and E. Girald; *Chemical Approaches to the Synthesis of Peptides and Proteins*, CRC Press, 1997. The cMBP peptides are best stored under inert atmosphere and kept in a freezer. When used in solution, it is best to avoid pH above 7 since that risks scrambling of the disulfide bridges.

A preferred bifunctional diaminedioxime chelator is Chelator 1, which has the Formula:

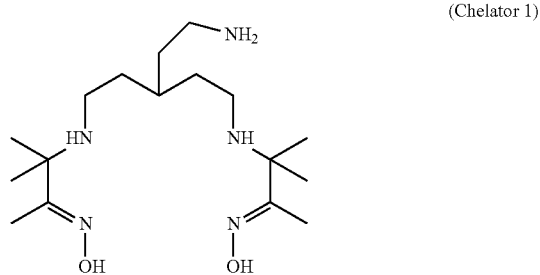 [SMILES: C/C(=N\O)C(C)(C)NCCC(CCN)CCNC(C)(C)/C(C)=N/O]

(Chelator 1)

wherein the bridgehead primary amine group is conjugated to L (i.e. the linker group) and/or cMBP peptide.

The diaminedioxime chelator of Formula III can be prepared by reaction of the appropriate diamine with either:
(i) the appropriate chloronitroso derivative Cl—C(E$^2$E$^3$)-CH(NO)E$^1$;
(ii) an alpha-chloro oxime of formula Cl—C(E$^2$E$^3$)-C(=NOH)E$^1$;
(iii) an alpha-bromoketone of formula Br—C(E$^2$E$^3$)-C(=O)E$^1$ followed by conversion of the diaminediketone product to the diaminedioxime with hydroxylamine.

Route (i) is described by S. Jurisson et al [Inorg. Chem., M, 3576-82 (1987)]. Chloronitroso compounds can be obtained by treatment of the appropriate alkene with nitrosyl chloride (NOCl) as is known in the art. Further synthetic details of chloronitroso compounds are given by: Ramalingam [Synth. Commun., 25(5), 743-752 (1995)]; Glaser [J. Org. Chem., 61(3), 1047-48 (1996)]; Clapp [J. Org. Chem., 36(8) 1169-70 (1971)]; Saito [Shizen Kagaku, 47, 41-49 (1995)] and Schulz [Z. Chem., 21(11), 404-405 (1981)] Route (iii) is described in broad terms by Nowotnik et al [Tetrahedron, 50(29), p. 8617-8632 (1994)]. Alpha-chloro-oximes can be obtained by oximation of the corresponding alpha-chloro-ketone or aldehyde, which are commercially available. Alpha-bromoketones are commercially available.

Further details of specific carboxy-functionalised and amine-functionalised chelators of the invention, and their conjugation to cMBP peptides, are provided in the supporting Examples.

In a third aspect, the present invention provides a method of preparation of the imaging agent of the first aspect, which comprises reaction of the chelator conjugate of Formula I of the first aspect with a supply of $^x$Tc as defined in the first aspect, in a suitable solvent.

Preferred aspects of the cMBP peptide and chelator in the chelator conjugate, and $^x$Tc in the third aspect are as described in the first aspect (above).

The suitable solvent is typically aqueous in nature, and is preferably a biocompatible carrier solvent as defined in the fourth aspect (below).

$^{99m}$Tc is commercially available from radioisotope generators, which provide [$^{99m}$Tc]-pertechnetate in sterile form. Methods of preparing technetium complexes are well known in the art [see eg. I. Zolle (Ed) *Technetium-99m Pharmaceuticals*, Springer, New York (2007)]. $^{94m}$Tc can be prepared and processed by the method of Bigott et al [Nucl. Med. Biol., 33(7), 923-933 (2006)].

In a fourth aspect, the present invention provides a radiopharmaceutical composition which comprises the imaging agent of the first aspect together with a biocompatible carrier, in a form suitable for mammalian administration.

Preferred aspects of the imaging agent in the fourth aspect are as defined in the first aspect. The term "in a form suitable for mammalian administration" is as defined above.

The "biocompatible carrier" is a fluid, especially a liquid, in which the imaging agent can be suspended or preferably dissolved, such that the composition is physiologically tolerable, i.e. can be administered to the mammalian body without toxicity or undue discomfort. The biocompatible carrier is suitably an injectable carrier liquid such as sterile, pyrogen-free water for injection; an aqueous solution such as saline (which may advantageously be balanced so that the final product for injection is isotonic); an aqueous buffer solution comprising a biocompatible buffering agent (e.g. phosphate buffer); an aqueous solution of one or more tonicity-adjusting substances (eg. salts of plasma cations with biocompatible counterions), sugars (e.g. glucose or sucrose), sugar alcohols (eg. sorbitol or mannitol), glycols (eg. glycerol), or other non-ionic polyol materials (eg. polyethyleneglycols, propylene glycols and the like). Preferably the biocompatible carrier is pyrogen-free water for injection, isotonic saline or phosphate buffer.

The imaging agents and biocompatible carrier are each supplied in suitable vials or vessels which comprise a sealed container which permits maintenance of sterile integrity and/or radioactive safety, plus optionally an inert headspace gas (eg. nitrogen or argon), whilst permitting addition and withdrawal of solutions by syringe or cannula. A preferred such container is a septum-sealed vial, wherein the gas-tight closure is crimped on with an overseal (typically of aluminium). The closure is suitable for single or multiple puncturing with a hypodermic needle (e.g. a crimped-on septum seal closure) whilst maintaining sterile integrity. Such containers have the additional advantage that the closure can withstand vacuum if desired (eg. to change the headspace gas or degas solutions), and withstand pressure changes such as reductions in pressure without permitting ingress of external atmospheric gases, such as oxygen or water vapour.

Preferred multiple dose containers comprise a single bulk vial (e.g. of 10 to 30 cm³ volume) which contains multiple patient doses, whereby single patient doses can thus be withdrawn into clinical grade syringes at various time intervals during the viable lifetime of the preparation to suit the clinical situation. Pre-filled syringes are designed to contain a single human dose, or "unit dose" and are therefore preferably a disposable or other syringe suitable for clinical use. The pharmaceutical compositions of the present invention preferably have a dosage suitable for a single patient and are provided in a suitable syringe or container, as described above.

The pharmaceutical composition may contain additional optional excipients such as: an antimicrobial preservative, pH-adjusting agent, filler, radioprotectant, solubiliser or osmolality adjusting agent.

By the term "antimicrobial preservative" is meant an agent which inhibits the growth of potentially harmful micro-organisms such as bacteria, yeasts or moulds. The antimicrobial preservative may also exhibit some bactericidal properties, depending on the dosage employed. The main role of the antimicrobial preservative(s) of the present invention is to inhibit the growth of any such micro-organism in the pharmaceutical composition. The antimicrobial preservative may, however, also optionally be used to inhibit the growth of potentially harmful micro-organisms in one or more components of kits used to prepare said composition prior to administration. Suitable antimicrobial preservative(s) include: the parabens, i.e. methyl, ethyl, propyl or butyl paraben or mixtures thereof; benzyl alcohol; phenol; cresol; cetrimide and thiomersal. Preferred antimicrobial preservative(s) are the parabens.

The term "pH-adjusting agent" means a compound or mixture of compounds useful to ensure that the pH of the composition is within acceptable limits (approximately pH 4.0 to 10.5, preferably 6.5 to 8.5 for the agents of the present invention) for human or mammalian administration. Suitable such pH-adjusting agents include pharmaceutically acceptable buffers, such as tricine, phosphate or TRIS [i.e. tris(hydroxymethyl)aminomethane], and pharmaceutically acceptable bases such as sodium carbonate, sodium bicarbonate or mixtures thereof. When the composition is employed in kit form, the pH adjusting agent may optionally be provided in a separate vial or container, so that the user of the kit can adjust the pH as part of a multi-step procedure.

By the term "filler" is meant a pharmaceutically acceptable bulking agent which may facilitate material handling during production and lyophilisation. Suitable fillers include inorganic salts such as sodium chloride, and water soluble sugars or sugar alcohols such as sucrose, maltose, mannitol or trehalose.

By the term "radioprotectant" is meant a compound which inhibits degradation reactions, such as redox processes, by trapping highly-reactive free radicals, such as oxygen-containing free radicals arising from the radiolysis of water. A combination of two or more different radioprotectants may be used. The radioprotectants of the present invention are suitably chosen from: ethanol; ascorbic acid; para-aminobenzoic acid (i.e. 4-aminobenzoic acid); gentisic acid (i.e. 2,5-dihydroxybenzoic acid), and where applicable salts of such acids with a biocompatible cation. By the term "biocompatible cation" ($B^c$) is meant a positively charged counterion which forms a salt with an ionised, negatively charged group, where said positively charged counterion is also non-toxic and hence suitable for administration to the mammalian body, especially the human body. Examples of suitable biocompatible cations include: the alkali metals sodium or potassium; the alkaline earth metals calcium and magnesium; and the ammonium ion. Preferred biocompatible cations are sodium and potassium, most preferably sodium. The radioprotectant of the present invention preferably comprises ascorbic acid or sodium ascorbate.

By the term "solubiliser" is meant an additive present in the composition which increases the solubility of the imaging agent in the solvent. A preferred such solvent is aqueous media, and hence the solubiliser preferably improves solubility in water. Suitable such solubilisers include: $C_{1-4}$ alcohols; glycerine; polyethylene glycol (PEG); propylene glycol; polyoxyethylene sorbitan monooleate; sorbitan monooleate; polysorbates; poly(oxyethylene)poly(oxypropylene)poly(oxyethylene) block copolymers (Pluronics™); cyclodextrins (e.g. alpha, beta or gamma cyclodextrin, hydroxypropyl-β-cyclodextrin or hydroxypropyl-γ-cyclodextrin) and lecithin. Preferred solubilisers are cyclodextrins, $C_{1-4}$ alcohols and Pluronics™, more preferably cyclodextrins and $C_{2-4}$ alcohols. When the solubiliser is an alcohol, it is preferably ethanol or propanol, more preferably ethanol. Ethanol has a potential dual role, since it can also function as a radioprotectant. When the solubiliser is a cyclodextrin, it is preferably a gamma cyclodextrin, more preferably hydroxypropyl-β-cyclodextrin (HPCD). The concentration of cyclodextrin can be from about 0.1 to about 40 mg/mL, preferably between about 5 and about 35 mg/mL, more preferably 20 to 30 mg/ml, most preferably around 25 mg/ml.

The radiopharmaceutical compositions of the present invention may be prepared by various methods:
 (i) aseptic manufacture techniques in which the radiometal complex formation is carried out in a clean room environment;
 (ii) terminal sterilisation, in which the radiometal complex formation is carried out without using aseptic manufacture and then sterilised at the last step [eg. by gamma irradiation, autoclaving dry heat or chemical treatment (e.g. with ethylene oxide)];
 (iii) kit methodology in which a sterile, non-radioactive kit formulation comprising the chelator conjugate of Formula I and optional excipients is reacted with a supply of the desired technetium radiometal.

Method (iii) is preferred, and kits for use in this method are described in the fifth embodiment (below).

Preferably, the imaging agent composition is chosen such that any unlabelled cMBP peptide is present in said composition at no more than 50 times the molar amount of the $^x$Tc-labelled cMBP peptide. Thus, the chemical excess of chelator conjugate used for $^x$Tc radiolabelling can be as high as a 1000-fold excess over the $^x$Tc, and the unlabelled conjugate may compete for c-Met sites in vivo. Low concentrations of chelator conjugate can, however, affect the RCP. Thus, for $^{99m}$Tc, RCP values of >90% can be achieved using 45 nanomoles of Compound 1, but varied between 70 and 95% when using 15-30 nanomoles. Any excess unlabelled peptide can be removed by HPLC or SPE.

By the term "unlabelled" is meant that the c-Met binding cyclic peptide is non-radioactive, i.e. is not radiolabelled with $^x$Tc, or any other radioisotope. Such unlabelled peptides primarily include the non-radioactive chelator conjugates of the second aspect (above). The term 'unlabelled' excludes the c-Met binding cyclic peptide labelled with $^{99}$Tc, where said $^{99}$Tc is present in the $^{99m}$Tc used to radiolabel said c-Met binding cyclic peptide and is thus a product of the same radiolabelling reaction. Preferably, the unlabelled c-Met binding cyclic peptide is present in said composition at less than 20, more preferably less than 10, most preferably less than 5 times the molar amount of the corresponding $^x$Tc-labelled peptide.

In a fifth aspect, the present invention provides a kit for the preparation of the radiopharmaceutical composition of the fourth aspect, which comprises the chelator conjugate of the second aspect in sterile, solid form such that upon reconstitution with a sterile supply of the radiometal in a biocompatible carrier, dissolution occurs to give the desired radiopharmaceutical composition.

Preferred aspects of the chelator conjugate in the fifth aspect are as described in the second aspect of the present invention (above).

By the term "kit" is meant one or more non-radioactive pharmaceutical grade containers, comprising the necessary chemicals to prepare the desired radiopharmaceutical composition, together with operating instructions. The kit is designed to be reconstituted with the desired radiometal to give a solution suitable for human administration with the minimum of manipulation.

The sterile, solid form is preferably a lyophilised solid. For $^{99m}$Tc, the kit is preferably lyophilised and is designed to be reconstituted with sterile $^{99m}$Tc-pertechnetate (TcO$_4^-$) from a $^{99m}$Tc radioisotope generator to give a solution suitable for human administration without further manipulation. Suitable kits comprise a container (eg. a septum-sealed vial) containing the chelator conjugate in either free base or acid salt form, together with a biocompatible reductant such as sodium dithionite, sodium bisulfite, ascorbic acid, formamidine sulfinic acid, stannous ion, Fe(II) or Cu(I). The biocompatible reductant is preferably a stannous salt such as stannous chloride or stannous tartrate. Alternatively, the kit may optionally contain a non-radioactive metal complex which, upon addition of the technetium, undergoes transmetallation (i.e. metal exchange) giving the desired product. The non-radioactive kits may optionally further comprise additional components such as a transchelator, radioprotectant, antimicrobial preservative, pH-adjusting agent or filler—as defined above.

In a sixth aspect, the present invention provides a method of imaging the human or animal body which comprises generating an image of at least a part of said body to which the imaging agent of the first aspect, or the radiopharmaceutical composition of the second aspect has distributed using PET or SPECT, wherein said imaging agent or composition has been previously administered to said body.

Preferred aspects of the imaging agent or composition in the sixth aspect are as described in the first and fourth aspects respectively of the present invention (above). Preferably, the radiopharmaceutical composition of the fourth aspect is used.

Preferably, the mammal is an intact mammalian body in vivo, and is more preferably a human subject. Preferably, the imaging agent can be administered to the mammalian body in a minimally invasive manner, i.e. without a substantial health risk to the mammalian subject even when carried out under professional medical expertise. Such minimally invasive administration is preferably intravenous administration into a peripheral vein of said subject, without the need for local or general anaesthetic.

The imaging of the sixth aspect is preferably of sites of c-Met over-expression or localisation. The site of c-Met over-expression or localisation is preferably a cancer or a precancerous lesion.

The imaging method of the sixth aspect may optionally be carried out repeatedly to monitor the effect of treatment of a human or animal body with a drug or radiation, said imaging being effected before and after said treatment, and optionally also during said treatment. Of particular interest is early monitoring of the efficacy of cancer therapy to ensure that malignant growth is controlled before the condition becomes terminal.

Included in this aspect is a method of diagnosis of sites of c-Met over-expression or localisation of the mammalian body in vivo, which comprises the imaging method of the sixth aspect.

In a seventh aspect, the present invention provides the use of the imaging agent of the first aspect, the radiopharmaceutical composition of the fourth aspect, or the kit of the fifth aspect, in a method of diagnosis of the human or animal body.

Preferred aspects of the imaging agent or composition in the seventh aspect are as described in the first and fourth aspects respectively of the present invention (above). The method of diagnosis of the seventh aspect preferably comprises the imaging method of the sixth aspect and preferred aspects thereof.

The invention is illustrated by the non-limiting Examples detailed below. Example 1 provides the synthesis of a cMBP peptide of the invention having metabolism inhibiting groups ($Z^1=Z^2=M^{IG}$) at both termini (Peptide 1). Examples 2 to 4 provide the synthesis of a bifunctional amine-functionalised chelator of the invention (Chelator 1). Example 5 provides the synthesis of a bifunctional active ester-functionalised chelator of the invention (Chelator 1A). Example 6 provides the synthesis of a chelator conjugate of a peptide of the invention (Peptide 1) with Chelator 1 ("Compound 1"). Example 7 provides the preparation of a $^{99m}$Tc complex of the invention ($^{99m}$Tc-Compound 1), and shows that the complexation proceeds efficiently in high radiochemical yield at room temperature. Example 8 provides the biodistribution of $^{99m}$Tc-Compound 1, and shows that the technetium complex exhibits useful tumour uptake, with good tumour:background ratios.

ABBREVIATIONS

Conventional single letter or 3-letter amino acid abbreviations are used.
% id: percentage injected dose
Ac: Acetyl
Acm: Acetamidomethyl
ACN: Acetonitrile
Boc: tert-Butyloxycarbonyl
tBu: tertiary-butyl
DCM: Dichloromethane
DMF: Dimethylformamide
DMSO: Dimethylsulfoxide
EDC: N-3-dimethylaminopropyl)-N'-ethylcarbodiimide.
Fmoc: 9-Fluorenylmethoxycarbonyl
HATU: O-(7-Azabenzotriazol-1-yl)-N,N,N',N'-tetramethyluronium hexafluorophosphate.
HBTU: O-Benzotriazol-1-yl-N,N,N',N'-tetramethyluronium hexafluorophosphate
HPLC: High performance liquid chromatography
HSPyU O—(N-succinimidyl)-N,N,N',N'-tetramethyleneuronium hexafluorophosphate
NETS: N-hydroxy-succinimide
NMM: N-Methylmorpholine
NMP: 1-Methyl-2-pyrrolidinone
Pbf: 2,2,4,6,7-Pentamethyldihydrobenzofuran-5-sulfonyl
PBS: Phosphate-buffered saline
PyBOP: benzotriazol-1-yl-oxytripyrrolidinophosphonium hexafluorophosphate
s.c.: sub-cutaneously,
tBu: tert-butyl TFA: Trifluoroacetic acid
THF: Tetrahydrofuran
TIS: Triisopropylsilane
Trt: Trityl.

COMPOUNDS OF THE INVENTION

| Name | Structure |
|---|---|
| Peptide 1 | Disulfide bridges at Cys4-16 and Cys6-14;<br>Ac-Ala-Gly-Ser-Cys-Tyr-Cys-Ser-Gly-Pro-Pro-Arg-Phe-Glu-Cys-Trp-Cys-Tyr-Glu-Thr-Glu-Gly-Thr-Gly-Gly-Gly-Lys-NH$_2$ or<br>Ac-AGSCYCSGPPRFECWCYETEGTGGGK-NH$_2$ |
| Chelator 1 | (structure) |
| Chelator 1A | (structure) |
| Compound 1 | [Peptide 1]-NH(CO)—(CH$_2$)$_3$—(CO)-[Chelator 1] | where:
Compound 1 is functionalised at the epsilon amine group of the carboxy terminal Lys of Peptide 1.

Example 1

Synthesis of Peptide 1

Step (a): Synthesis of Protected Precursor Linear Peptide.
The precursor linear peptide has the structure:

Ac-Ala-Gly-Ser-Cys-Tyr-Cys(Acm)-Ser-Gly-Pro-Pro-
Arg-Phe-Glu-Cys(Acm)-Trp-Cys-Tyr-Glu-Thr-Glu-Gly-
Thr-Gly-Gly-Gly-Lys-NH$_2$

The peptidyl resin H-Ala-Gly-Ser(tBu)-Cys(Trt)-Tyr(tBu)-Cys(Acm)-Ser(tBu)-Gly-Pro-Pro-Arg(Pbf)-Phe-Glu(OtBu)-Cys(Acm)-Trp(Boc)-Cys(Trt)-Tyr(tBu)-Glu(OtBu)-Thr(ψ$^{Me,Me}$pro)-Glu(OtBu)-Gly-Thr(tBu)-Gly-Gly-Gly-Lys(Boc)-Polymer was assembled on an Applied Biosystems 433A peptide synthesizer using Fmoc chemistry starting with 0.1 mmol Rink Amide Novagel resin. An excess of 1 mmol pre-activated amino acids (using HBTU) was applied in the coupling steps. Glu-Thr pseudoproline (Novabiochem 05-20-1122) was incorporated in the sequence. The resin was transferred to a nitrogen bubbler apparatus and treated with a solution of acetic anhydride (1 mmol) and NMM (1 mmol) dissolved in DCM (5 mL) for 60 min. The anhydride solution was removed by filtration and the resin washed with DCM and dried under a stream of nitrogen.

The simultaneous removal of the side-chain protecting groups and cleavage of the peptide from the resin was carried out in TFA (10 mL) containing 2.5% TIS, 2.5% 4-thiocresol and 2.5% water for 2 hours and 30 min. The resin was removed by filtration, TFA removed in vacuo and diethyl ether added to the residue. The formed precipitate was washed with diethyl ether and air-dried affording 264 mg of crude peptide.

Purification by preparative HPLC (gradient: 20-30% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 30 min) of the crude peptide afforded 100 mg of pure Peptide I linear precursor. The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 6.54 min). Further product characterisation was carried out using electrospray mass spectrometry (MH$_2^{2+}$ calculated: 1464.6, MH$_2^{2+}$ found: 1465.1).

Step (b): Formation of Monocyclic Cys4-16 Disulfide Bridge.

Cys4-16; Ac-Ala-Gly-Ser-Cys-Tyr-Cys(Acm)-Ser-Gly-
Pro-Pro-Arg-Phe-Glu-Cys(Acm)-Trp-Cys-Tyr-Glu-Thr-
Glu-Gly-Thr-Gly-Gly-Gly-Lys-NH$_2$

The linear precursor from step (a) (100 mg) was dissolved in 5% DMSO/water (200 mL) and the solution adjusted to pH 6 using ammonia. The reaction mixture was stirred for 5 days. The solution was then adjusted to pH 2 using TFA and most of the solvent removed by evaporation in vacuo. The residue (40 mL) was injected in portions onto a preparative HPLC column for product purification.

Purification by preparative HPLC (gradient: 0% B for 10 min, then 0-40% B over 40 min where A=H$_2$O/0.1% TFA and B=ACN/0.1% TFA, flow rate: 10 mL/min, column: Phenomenex Luna 5µ C18 (2) 250×21.20 mm, detection: UV 214 nm, product retention time: 44 min) of the residue afforded 72 mg of pure Peptide 1 monocyclic precursor. The pure product (as a mixture of isomers P1 to P3) was analysed by analytical HPLC (gradient: 10-40% B over 10 min where A=H$_2$O/0.1% TFA and B=ACN/0.1% TFA, flow rate: 0.3 mL/min, column: Phenomenex Luna 3µ C18 (2) 50×2 mm, detection: UV 214 nm, product retention time: 5.37 min (P1); 5.61 min (P2); 6.05 min (P3)). Further product characterisation was carried out using electrospray mass spectrometry (MH$_2^{2+}$ calculated: 1463.6, MH$_2^{2+}$ found: 1464.1 (P1); 1464.4 (P2); 1464.3 (P3)).

Step (c): Formation of Second Cys6-14 Disulfide Bridge (Peptide 1).

The monocyclic precursor from step (b) (72 mg) was dissolved in 75% AcOH/water (72 mL) under a blanket of nitrogen. 1 M HCl (7.2 mL) and 0.05 M I$_2$ in AcOH (4.8 mL) were added in that order and the mixture stirred for 45 min. 1 M ascorbic acid (1 mL) was added giving a colourless mixture. Most of the solvents were evaporated in vacuo and the residue (18 mL) diluted with water/0.1 TFA (4 mL) and the product purified using preparative HPLC. Purification by preparative HPLC (gradient: 0% B for 10 min, then 20-30% B over 40 min where A=H$_2$O/0.1% TFA and B=ACN/0.1% TFA, flow rate: 10 mL/min, column: Phenomenex Luna 5µ C18 (2)

250×21.20 mm, detection: UV 214 nm, product retention time: 43-53 min) of the residue afforded 52 mg of pure Peptide 1. The pure product was analysed by analytical HPLC (gradient: 10-40% B over 10 min where A=H$_2$O/0.1% TFA and B=ACN/0.1% TFA, flow rate: 0.3 mL/min, column: Phenomenex Luna 3μ C18 (2) 50×2 mm, detection: UV 214 nm, product retention time: 6.54 min). Further product characterisation was carried out using electrospray mass spectrometry (MH$_2^{2+}$ calculated: 1391.5, MH$_2^{2+}$ found: 1392.5).

Example 2

Synthesis of 1,1,1-tris(2-aminoethyl)methane

Step. 1(a): 3(methoxycarbonylmethylene)glutaric acid dimethylester.

Carbomethoxymethylenetriphenylphosphorane (167 g, 0.5 mol) in toluene (600 ml) was treated with dimethyl 3-oxoglutarate (87 g, 0.5 mol) and the reaction heated to 100° C. on an oil bath at 120° C. under an atmosphere of nitrogen for 36 h. The reaction was then concentrated in vacuo and the oily residue triturated with 40/60 petrol ether/diethylether 1:1, 600 ml. Triphenylphosphine oxide precipitated out and the supernatant liquid was decanted/filtered off. The residue on evaporation in vacuo was Kugelrohr distilled under high vacuum Bpt (oven temperature 180-200° C. at 0.2 torr) to give 3-(methoxycarbonylmethylene)glutaric acid dimethylester (89.08 g, 53%).

NMR $^1$H (CDCl$_3$): δ 3.31 (2H, s, CH$_2$), 3.7 (9H, s, 3×OCH$_3$), 3.87 (2H, s, CH$_2$), 5.79 (1H, s, =CH,) ppm.

NMR $^{13}$C (CDCl$_3$), δ 36.56, CH$_3$, 48.7, 2×CH$_3$, 52.09 and 52.5 (2×CH$_2$); 122.3 and 146.16 C=CH; 165.9, 170.0 and 170.5 3×COO ppm.

Step 1(b): (Hydrogenation of 3-methoxycarbonylmethylene) glutaric acid dimethylester.

3-(Methoxycarbonylmethylene)glutaric acid dimethylester (89 g, 267 mmol) in methanol (200 ml) was shaken with (10% palladium on charcoal: 50% water) (9 g) under an atmosphere of hydrogen gas (3.5 bar) for (30 h). The solution was filtered through kieselguhr and concentrated in vacuo to give 3-(methoxycarbonylmethyl)glutaric acid dimethylester as an oil, yield (84.9 g, 94%).

NMR $^1$H (CDCl$_3$), δ 2.48 (6H, d, J=8 Hz, 3×CH$_2$), 2.78 (1H, hextet, J=8 Hz CH,) 3.7 (9H, s, 3×CH$_3$).

NMR $^{13}$C (CDCl$_3$), δ 28.6, CH; 37.50, 3×CH$_3$; 51.6, 3×CH$_2$; 172.28, 3×COO.

Step 1(c): Reduction and Esterification of Trimethyl Ester to the Triacetate.

Under an atmosphere of nitrogen in a 3 necked 2 L round bottomed flask lithium aluminium hydride (20 g, 588 mmol) in THF (400 ml) was treated cautiously with tris(methyloxycarbonylmethyl)methane (40 g, 212 mmol) in THF (200 ml) over 1 h. A strongly exothermic reaction occurred, causing the solvent to reflux strongly. The reaction was heated on an oil bath at 90° C. at reflux for 3 days. The reaction was quenched by the cautious dropwise addition of acetic acid (100 ml) until the evolution of hydrogen ceased. The stirred reaction mixture was cautiously treated with acetic anhydride solution (500 ml) at such a rate as to cause gentle reflux. The flask was equipped for distillation and stirred and then heating at 90° C. (oil bath temperature) to distil out the THF. A further portion of acetic anhydride (300 ml) was added, the reaction returned to reflux configuration and stirred and heated in an oil bath at 140° C. for 5 h. The reaction was allowed to cool and filtered. The aluminium oxide precipitate was washed with ethyl acetate and the combined filtrates concentrated on a rotary evaporator at a water bath temperature of 50° C. in vacuo (5 mmHg) to afford an oil. The oil was taken up in ethyl acetate (500 ml) and washed with saturated aqueous potassium carbonate solution. The ethyl acetate solution was separated, dried over sodium sulfate, and concentrated in vacuo to afford an oil. The oil was Kugelrohr distilled in high vacuum to give tris(2-acetoxyethyl)methane (45.3 g, 95.9%) as an oil. Bp. 220° C. at 0.1 mmHg.

NMR $^1$H (CDCl$_3$), δ 1.66 (7H, m, 3×CH$_2$, CH), 2.08 (1H, s, 3×CH$_3$); 4.1 (6H, t, 3×CH$_2$O).

NMR $^{13}$C (CDCl$_3$), δ 20.9, CH$_3$; 29.34, CH; 32.17, CH$_2$; 62.15, CH$_2$O; 171, CO.

Step 1 (d): Removal of Acetate Groups from the Triacetate.

Tris(2-acetoxyethyl)methane (45.3 g, 165 mM) in methanol (200 ml) and 880 ammonia (100 ml) was heated on an oil bath at 80° C. for 2 days. The reaction was treated with a further portion of 880 ammonia (50 ml) and heated at 80° C. in an oil bath for 24 h. A further portion of 880 ammonia (50 ml) was added and the reaction heated at 80° C. for 24 h. The reaction was then concentrated in vacuo to remove all solvents to give an oil. This was taken up into 880 ammonia (150 ml) and heated at 80° C. for 24 h. The reaction was then concentrated in vacuo to remove all solvents to give an oil. Kugelrohr distillation gave acetamide by 170-180 0.2 mm. The bulbs containing the acetamide were washed clean and the distillation continued. Tris(2-hydroxyethyl)methane (22.53 g, 92%) distilled at by 220° C. 0.2 mm.

NMR $^1$H (CDCl$_3$), δ 1.45 (6H, q, 3×CH$_2$), 2.2 (1H, quintet, CH); 3.7 (6H, t 3×CH$_2$OH); 5.5 (3H, brs, 3×OH).

NMR $^{13}$C (CDCl$_3$), δ 22.13, CH; 33.95, 3×CH$_2$; 57.8, 3×CH$_2$OH.

Step 1(e): Conversion of the Triol to the Tris(Methanesulfonate).

To an stirred ice-cooled solution of tris(2-hydroxyethyl) methane (10 g, 0.0676 mol) in dichloromethane (50 ml) was slowly dripped a solution of methanesulfonyl chloride (40 g, 0.349 mol) in dichloromethane (50 ml) under nitrogen at such a rate that the temperature did not rise above 15° C. Pyridine (21.4 g, 0.27 mol, 4 eq) dissolved in dichloromethane (50 ml) was then added drop-wise at such a rate that the temperature did not rise above 15° C., exothermic reaction. The reaction was left to stir at room temperature for 24 h and then treated with 5N hydrochloric acid solution (80 ml) and the layers separated. The aqueous layer was extracted with further dichloromethane (50 ml) and the organic extracts combined, dried over sodium sulfate, filtered and concentrated in vacuo to give tris[2-(methylsulfonyloxy)ethyl]methane contaminated with excess methanesulfonyl chloride. The theoretical yield was 25.8 g.

NMR $^1$H (CDCl$_3$), δ 4.3 (6H, t, 2×CH$_2$), 3.0 (9H, s, 3×CH$_3$), 2 (1H, hextet, CH), 1.85 (6H, q, 3×CH$_2$).

Step 1(f): Preparation of 1,1,1-tris(2-azidoethyl)methane.

A stirred solution of tris[2-(methylsulfonyloxy)ethyl] methane [from Step 1(e), contaminated with excess methylsulfonyl chloride] (25.8 g, 67 mmol, theoretical) in dry DMF (250 ml) under nitrogen was treated with sodium azide (30.7 g, 0.47 mol) portion-wise over 15 minutes. An exotherm was observed and the reaction was cooled on an ice bath. After 30 minutes, the reaction mixture was heated on an oil bath at 50° C. for 24 h. The reaction became brown in colour. The reaction was allowed to cool, treated with dilute potassium carbonate solution (200 ml) and extracted three times with 40/60 petrol ether/diethylether 10:1 (3×150 ml). The organic extracts were washed with water (2×150 ml), dried over sodium sulfate and filtered. Ethanol (200 ml) was added to the petrol/ether solution to keep the triazide in solution and the volume reduced in vacuo to no less than 200 ml. Ethanol (200 ml) was added and reconcentrated in vacuo to remove the last traces of petrol leaving no less than 200 ml of ethanolic solution. The ethanol solution of triazide was used directly in Step 1(g).
CARE: DO NOT REMOVE ALL THE SOLVENT AS THE AZIDE IS POTENTIALLY EXPLOSIVE AND SHOULD BE KEPT IN DILUTE SOLUTION AT ALL TIMES.

Less than 0.2 ml of the solution was evaporated in vacuum to remove the ethanol and an NMR run on this small sample: NMR $^1$H (CDCl$_3$), δ 3.35 (6H, t, 3×CH$_2$), 1.8 (1H, septet, CH,), 1.6 (6H, q, 3×CH$_2$).

Step 1(g): Preparation of 1,1,1-tris(2-aminoethyl)methane.

Tris(2-azidoethyl)methane (15.06 g, 0.0676 mol), (assuming 100% yield from previous reaction) in ethanol (200 ml) was treated with 10% palladium on charcoal (2 g, 50% water) and hydrogenated for 12 h. The reaction vessel was evacuated every 2 hours to remove nitrogen evolved from the reaction and refilled with hydrogen. A sample was taken for NMR analysis to confirm complete conversion of the triazide to the triamine. Caution: unreduced azide could explode on distillation. The reaction was filtered through a celite pad to remove the catalyst and concentrated in vacuo to give tris(2-aminoethyl)methane as an oil. This was further purified by Kugelrohr distillation bp. 180-200° C. at 0.4 mm/Hg to give a colourless oil (8.1 g, 82.7% overall yield from the triol).

NMR $^1$H (CDCl$_3$), δ 2.72 (6H, t, 3×CH$_2$N), 1.41 (H, septet, CH), 1.39 (6H, q, 3×CH$_2$).

NMR $^{13}$C (CDCl$_3$), δ 39.8 (CH$_2$NH$_2$), 38.2 (CH$_2$.), 31.0 (CH).

Example 3

Preparation of 3-chloro-3-methyl-2-nitrosobutane

A mixture of 2-methylbut-2-ene (147 ml, 1.4 mol) and isoamyl nitrite (156 ml, 1.16 mol) was cooled to −30° C. in a bath of cardice and methanol and vigorously stirred with an overhead air stirrer and treated dropwise with concentrated hydrochloric acid (140 ml, 1.68 mol) at such a rate that the temperature was maintained below −20° C. This requires about 1 h as there is a significant exotherm and care must be taken to prevent overheating. Ethanol (100 ml) was added to reduce the viscosity of the slurry that had formed at the end of the addition and the reaction stirred at −20 to −10° C. for a further 2 h to complete the reaction. The precipitate was collected by filtration under vacuum and washed with 4×30 ml of cold (−20° C.) ethanol and 100 ml of ice cold water, and dried in vacuo to give 3-chloro-3-methyl-2-nitrosobutane as a white solid. The ethanol filtrate and washings were combined and diluted with water (200 ml) and cooled and allowed to stand for 1 h at −10° C. when a further crop of 3-chloro-3-methyl-2-nitrosobutane crystallised out. The precipitate was collected by filtration and washed with the minimum of water and dried in vacuo to give a total yield of 3-chloro-3-methyl-2-nitrosobutane (115 g 0.85 mol, 73%)>98% pure by NMR.

NMR $^1$H (CDCl$_3$), As a mixture of isomers (isomer1, 90%) 1.5 d, (2H, CH$_3$), 1.65 d, (4H, 2×CH$_3$), 5.85, q, and 5.95, q, together 1H. (isomer2, 10%), 1.76 s, (6H, 2×CH$_3$), 2.07 (3H, CH$_3$).

Example 4

Synthesis of bis[N-(1,1-dimethyl-2-N-hydroxyimine propyl)-2-aminoethyl]-(2-aminoethyl)methane (Chelator 1)

To a solution of tris(2-aminoethyl)methane (4.047 g, 27.9 mmol) in dry ethanol (30 ml) was added potassium carbonate anhydrous (7.7 g, 55.8 mmol, 2 eq) at room temperature with vigorous stirring under a nitrogen atmosphere. A solution of 3-chloro-3-methyl-2-nitrosobutane (7.56 g, 55.8 mol, 2 eq) was dissolved in dry ethanol (100 ml) and 75 ml of this solution was dripped slowly into the reaction mixture. The reaction was followed by TLC on silica [plates run in dichloromethane, methanol, concentrated (0.88 sg) ammonia; 100/30/5 and the TLC plate developed by spraying with ninhydrin and heating]. The mono-, di- and tri-alkylated products were seen with RF's increasing in that order. Analytical HPLC was run using PRP reverse phase column in a gradient of 7.5-75% acetonitrile in 3% aqueous ammonia. The reaction was concentrated in vacuo to remove the ethanol and resuspended in water (110 ml). The aqueous slurry was extracted with ether (100 ml) to remove some of the trialkylated compound and lipophilic impurities leaving the mono and desired dialkylated product in the water layer. The aqueous solution was buffered with ammonium acetate (2 eq, 4.3 g, 55.8 mmol) to ensure good chromatography. The aqueous solution was stored at 4° C. overnight before purifying by automated preparative HPLC.

Yield (2.2 g, 6.4 mmol, 23%).

Mass spec; Positive ion 10 V cone voltage. Found: 344; calculated M+H=344.

NMR $^1$H (CDCl$_3$), δ 1.24 (6H, s, 2×CH$_3$), 1.3 (6H, s, 2×CH$_3$), 1.25-1.75 (7H, m, 3×CH$_2$, CH), (3H, s, 2×CH$_2$), 2.58 (4H, m, CH$_2$N), 2.88 (2H, t CH$_2$N$_2$), 5.0 (6H, s, NH$_2$, 2×NH, 2×OH).

NMR $^1$H ((CD$_3$)$_2$SO) δ1.1 4×CH; 1.29, 3×CH$_2$; 2.1 (4H, t, 2×CH$_2$);

NMR $^{13}$C ((CD$_3$)$_2$SO), δ 9.0 (4×CH$_3$), 25.8 (2×CH$_3$), 31.0 2×CH$_2$, 34.6 CH$_2$, 56.8 2×CH$_2$N; 160.3, C═N.

HPLC conditions: flow rate 8 ml/min using a 25 mm PRP column [A=3% ammonia solution (sp. gr=0.88)/water; B=Acetonitrile].

|  |  | Time (min) | | | | |
| --- | --- | --- | --- | --- | --- | --- |
|  |  | 0 | 15 | 20 | 22 | 30 |
| Gradient | % B | 7.5 | 75.0 | 75.0 | 7.5 | 7.5 |

Load 3 ml of aqueous solution per run, and collect in a time window of 12.5-13.5 min.

Example 5

Synthesis of Tetrafluorothiophenyl Ester of Chelator 1-Glutaric Acid (Chelator 1A)

a) Synthesis of [Chelator 1]-Glutaric Acid Intermediate

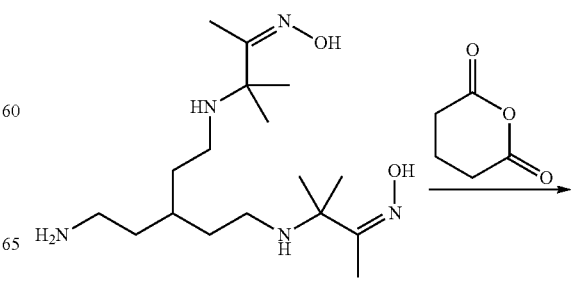

-continued

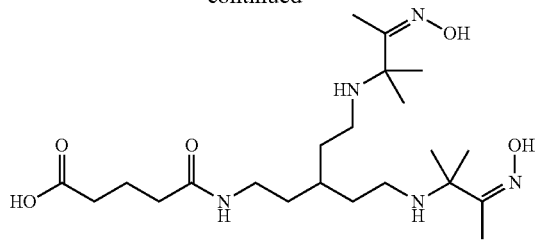

Chelator 1 (100 mg, 0.29 mmol) was dissolved in DMF (10 mL) and glutaric anhydride (33 mg, 0.29 mmol) added by portions with stirring. The reaction was stirred for 23 hours to afford complete conversion to the desired product. The pure acid was obtained following RP-HPLC in good yield.

b) Synthesis of Chelator 1A

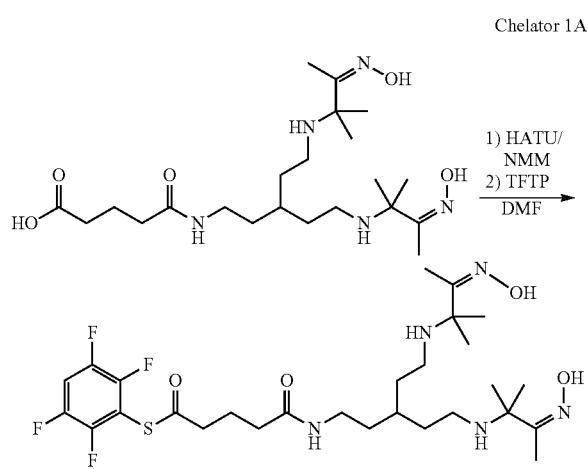

To [Chelator 1]-glutaric acid (from Step a; 300 mg, 0.66 mmol) in DMF (2 mL) was added HATU (249 mg, 0.66 mmol) and NMM (132 µL, 1.32 mmol). The mixture was stirred for 5 minutes then tetrafluorothiophenol (0.66 mmol, 119 mg) was added. The solution was stirred for 10 minutes then the reaction mixture was diluted with 20% acetonitrile/water (8 mL) and the product purified by RP-HPLC yielding 110 mg of the desired product following freeze-drying.

Example 6

Synthesis of Peptide 1 Conjugate with Chelator 1 (Compound 1)

Chelator 1A (3.8 mg, Example 5), Peptide 1 (3.4 mg) and sym.-collidine (1.6 µL) were dissolved in DMF (1 mL) and the solution stirred for 90 min. The reaction mixture was diluted with water (6 mL) and the product purified using preparative HPLC.

Purification by preparative HPLC (10-20% B over 40 min where A=$H_2O$/0.1% TFA and B=ACN/0.1% TFA, flow rate: 10 mL/min, column: Phenomenex Luna 5µ C18 (2) 250×21.20 mm, detection: UV 214 nm) of the crude peptide afforded 1.1 mg (28%) pure Compound 1. The purified material was analysed by analytical HPLC (gradient: 10-40% B over 5 min where A=$H_2O$/0.1% TFA and B=ACN/0.1% TFA, flow rate: 0.6 mL/min, column: Phenomenex Luna 3µ C18 (2) 20×2 mm, detection: UV 214 nm, $t_R$: 3.04 min). Further product characterisation was carried out using electrospray mass spectrometry (found m/z: 1611.2, expected $MH_2^{2+}$: 1611.2).

Example 7

$^{99m}$Tc-Radiolabelling of Compound 1

Step (i): Lyophilised Vials.

Compound 1 (45 nmol) was lyophilised in a first vial (Vial 1). A lyophilised kit containing the following formulation (Vial 2) was prepared separately:

| Component | M. Wt | mg | µmoles |
|---|---|---|---|
| $SnCl_2 \cdot 2H_2O$ | 225.63 | 0.016 | 0.07 |
| $MDP(H_4)$ | 176.00 | 0.025 | 0.14 |
| $NaHCO_3$ | 84.01 | 4.5 | 53.6 |
| $Na_2CO_3$ | 105.99 | 0.6 | 5.66 |
| NaPABA | 159.12 | 0.20 | 1.26 |

Step (ii): Radiolabelling.

Vial 1 was reconstituted with a water:ethanol solution (0.1 mL of a 50:50 mixture), and the vial sonicated or mixed for 10 minutes. The resulting solution of Compound 1 (0.1 mL) was then added to Vial 2. $^{99m}$Tc-pertechnetate eluate from a Drytec™ generator (GE Healthcare; 0.9 ml, 0.25-2.18 GBq) was then added to the vial, and the solution allowed to stand at room temperature for 20 min before HPLC analysis. The RCP was 93 to 94%.

Example 8

Biodistribution of $^{99m}$Tc-Compound 1 in Tumour-Bearing Nude Mice

CD-1 male nude mice (ca. 20 g) were housed in individual ventilated cages, with ad libitum access to food and water. HT-29 cells (ATCC, Cat. no. HTB-38) were grown in McCoy's 5a medium (Sigma # M8403) supplemented with 10% fetal bovine serum and penicillin/streptomycin. Cells were split 1:3 two times a week, at 70-80% confluent using 0.25% trypsin and incubated in 5% $CO_2$ at 37° C. The mice were injected s.c under light gas anaesthesia (Isoflurane) with the HT-29 cell suspension at one site (nape of the neck) with a nominal dose of $10^6$ cells per injections in a volume of 100 µl using a fine bore needle (25 G). The tumours were then allowed to develop for 20 days, or until at least 200 $mm^3$ in volume (for inclusion in the study).

After the 20 day growth time, animals were injected with $^{99m}$Tc-Compound 1 (0.1 ml, 1-5 MBq/animal), as an intravenous bolus via the tail vein. At various times post injection animals were euthanised, dissected and the following organs and tissues removed. The results at 120 min p.i. were as follows:

| Percentage injected dose (% id/g) | | | | | Ratio (Tumour:background) | | | |
|---|---|---|---|---|---|---|---|---|
| Blood | Tumour | Lung | Liver | Muscle | T:blood | T:lung | T:liver | T:muscle |
| 0.29 (0.1) | 1.08 (0.1) | 0.37 (0.0) | 0.46 (0.1) | 0.11 (0.1) | 3.7 | 2.9 | 2.4 | 12.2 |

44% of activity retained in the body at 120 min p.i. was present in the tumour.

What is claimed is:

1. An imaging agent which comprises a radioactive $^xTc$ complex of a chelator conjugate of a c-Met binding peptide, said chelator conjugate being of Formula I:

$$Z^1\text{-[cMBP]-}Z^2 \qquad (I)$$

where:

$^xTc$ is the radioisotope $^{94m}Tc$ or $^{99m}Tc$;

cMBP is an 18 to 30-mer c-Met binding cyclic peptide of Formula II:

$$\text{-(A)}_x\text{-Q-(A')}_y\text{-} \qquad (II)$$

where Q is the amino acid sequence (SEQ-1): -Cys$^a$-X$^1$-Cys$^c$-X$^2$-Gly-Pro-Pro-X$^3$-Phe-Glu-Cys$^d$-Trp-Cys$^b$-Tyr-X$^4$-X$^5$-X$^6$- wherein X$^1$ is Asn, His or Tyr;

X$^2$ is Gly, Ser, Thr or Asn;

X$^3$ is Thr or Arg;

X$^4$ is Ala, Asp, Glu, Gly or Ser;

X$^5$ is Ser or Thr;

X$^6$ is Asp or Glu;

and Cys$^{a-d}$ are each cysteine residues such that residues a and b as well as c and d are cyclised to form two separate disulfide bonds;

one of A and A' is any amino acid other than Cys, and the other one of A or A' is a linker peptide selected from: -Gly-Gly-Gly-Lys- (SEQ-4), -Gly-Ser-Gly-Lys- (SEQ-5) or -Gly-Ser-Gly-Ser-Lys- (SEQ-6) wherein a $Z^3$ group is attached to the epsilon amine group of the Lys residue of said linker peptide and $Z^3$ is conjugated to $^xTc$;

x and y are independently integers of value 0 to 13, and are selected such that [x+y]=1 to 13;

$Z^1$ is attached to the N-terminus of cMBP, and is —NH(C=O)R$^G$ where —(C=O)R$^G$ has R$^G$ selected from: C$_{1-6}$alkyl, or C$_{3-10}$ aryl groups or comprises a polyethyleneglycol (PEG) building block;

$Z^2$ is attached to the C-terminus of cMBP and is a primary amide;

$Z^3$ is a chelator of Formula (III):

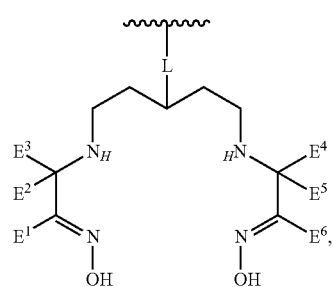

(III)

wherein E$^1$-E$^6$ are each independently an R' group;

each R' is independently H or C$_{1-4}$ alkyl, C$_{3-7}$ alkylaryl, C$_{2-7}$ alkoxyalkyl, C$_{1-4}$ hydroxyalkyl, C$_{1-4}$ fluoroalkyl, C$_{2-7}$ carboxyalkyl or C$_{1-4}$ aminoalkyl, or two or more R' groups together with the atoms to which they are attached form a carbocyclic, heterocyclic, saturated or unsaturated ring;

L is a synthetic linker group of formula -(A")$_m$- wherein each A" is independently —CR2-, —CR=CR—, —C≡C—, —CR$_2$CO$_2$—, —CO$_2$CR$_2$—, —NRCO—, —CONR—, —NR(C=O)NR—, —NR(C=S)NR—, —SO$_2$NR—, —NRSO$_2$—, —CR2OCR2-, —CR$_2$SCR$_2$—, —CR$_2$NRCR$_2$—, a C$_{4-8}$ cycloheteroalkylene group, a C$_{4-8}$ cycloalkylene group, a C$_{5-12}$ arylene group, or a C$_{3-12}$ heteroarylene group, or a monodisperse polyethyleneglycol (PEG) building block;

each R is independently selected from H, C$_{1-4}$ alkyl, C$_{2-4}$ alkenyl, C$_{2-4}$ alkynyl, C$_{1-4}$ alkoxyalkyl or C$_{1-4}$ hydroxyalkyl; and m is an integer of value 1 to 10.

2. The imaging agent of claim 1, wherein Q comprises the amino acid sequence of either SEQ-2 or SEQ-3:

```
                                                      (SEQ-2)
Ser-Cys^a-X^1-Cys^c-X^2-Gly-Pro-Pro-X^3-Phe-Glu-Cys^d-

Trp-Cys^b-Tyr-X^4-X^5-X^6;

(SEQ-3)
Ala-Gly-Ser-Cys^a-X^1-Cys^c-X^2-Gly-Pro-Pro-X^3-Phe-

Glu-Cys^d-Trp-Cys^b-Tyr-X^4-X^5-X^6-Gly-Thr.
```

3. The imaging agent of claim 1, wherein X$^3$ is Arg.

4. The imaging agent of claim 1, where cMBP has the amino acid sequence (SEQ-7):

Ala-Gly-Ser-Cys$^a$-Tyr-Cys$^c$-Ser-Gly-Pro-Pro-Arg-Phe-Glu-Cys$^d$-Trp-Cys$^b$-Tyr-Glu-Thr-Glu-Gly-Thr-Gly-Gly-Gly-Lys.

5. The imaging agent of claim 1, where the chelator is of Formula IIIA:

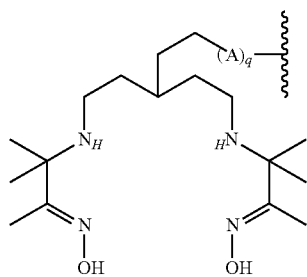

(IIIA)

where q is an integer of value 1 to 6, and A" is as defined for Formula III.

6. The imaging agent of claim 1, where $^x$Tc is $^{99m}$Tc.

7. A method of preparation of the imaging agent of claim 1 which comprises reacting the chelator conjugate with $^x$Tc as defined in claim 1.

8. A radiopharmaceutical composition comprising the imaging agent of claim 1 together with a pharmaceutically acceptable carrier.

9. A kit for the preparation of a radiopharmaceutical composition which comprises the chelator conjugate of claim 1 in sterile, solid form.

10. A method of imaging a mammalian body comprising administering to said body the imaging agent of claim 1, or the radiopharmaceutical composition of claim 8, and generating an image of at least a part of said body using PET or SPECT.

11. The method of claim 10 wherein the images are of sites of c-Met overexpression or localization.

12. The method of claim 11 wherein the site of c-Met overexpression or localization is a cancer or precancerous lesion.

13. The method of claim 10 which is performed repeatedly to monitor the efficacy of cancer therapy of a human or animal body administered a drug or radiation, said imaging occurring before, after, and optionally during said drug or radiation administration.

* * * * *

SEQUENCE LISTING

<160> NUMBER OF SEQ ID NOS: 7

<210> SEQ ID NO 1
<211> LENGTH: 17
<212> TYPE: PRT
<213> ORGANISM: Artificial
<220> FEATURE:
<223> OTHER INFORMATION: synthetic peptide
<220> FEATURE:
<221> NAME/KEY: DISULFID
<222> LOCATION: (1)..(13)
<220> FEATURE:
<221> NAME/KEY: MISC_FEATURE
<222> LOCATION: (1)..(1)
<223> OTHER INFORMATION: metabolism inhibiting group or chelator
      attached
<220> FEATURE:
<221> NAME/KEY: VARIANT
<222> LOCATION: (2)..(2)
<223> OTHER INFORMATION: N, H or Y
<220> FEATURE:
<221> NAME/KEY: DISULFID
<222> LOCATION: (3)..(11)
<220> FEATURE:
<221> NAME/KEY: VARIANT
<222> LOCATION: (4)..(4)
<223> OTHER INFORMATION: G, S, T or N
<220> FEATURE:
<221> NAME/KEY: VARIANT
<222> LOCATION: (8)..(8)
<223> OTHER INFORMATION: T or R
<220> FEATURE:
<221> NAME/KEY: VARIANT
<222> LOCATION: (15)..(15)
<223> OTHER INFORMATION: A, D, E, G or S
<220> FEATURE:
<221> NAME/KEY: VARIANT
<222> LOCATION: (16)..(16)
<223> OTHER INFORMATION: S or T
<220> FEATURE:
<221> NAME/KEY: MISC_FEATURE
<222> LOCATION: (17)..(17)
<223> OTHER INFORMATION: metabolism inhibiting group or chelator
      attached
<220> FEATURE:
<221> NAME/KEY: VARIANT
<222> LOCATION: (17)..(17)
<223> OTHER INFORMATION: D or E

<400> SEQUENCE: 1

Cys Xaa Cys Xaa Gly Pro Pro Xaa Phe Glu Cys Trp Cys Tyr Xaa Xaa
1               5                   10                  15

Xaa

<210> SEQ ID NO 2
<211> LENGTH: 18
<212> TYPE: PRT
<213> ORGANISM: Artificial
<220> FEATURE:
<223> OTHER INFORMATION: synthetic peptide

```
<220> FEATURE:
<221> NAME/KEY: MISC_FEATURE
<222> LOCATION: (1)..(1)
<223> OTHER INFORMATION: metabolism inhibiting group or chelator
      attached
<220> FEATURE:
<221> NAME/KEY: DISULFID
<222> LOCATION: (2)..(14)
<220> FEATURE:
<221> NAME/KEY: VARIANT
<222> LOCATION: (3)..(3)
<223> OTHER INFORMATION: N, H OR Y
<220> FEATURE:
<221> NAME/KEY: DISULFID
<222> LOCATION: (4)..(12)
<220> FEATURE:
<221> NAME/KEY: VARIANT
<222> LOCATION: (5)..(5)
<223> OTHER INFORMATION: G, S, T or N
<220> FEATURE:
<221> NAME/KEY: VARIANT
<222> LOCATION: (9)..(9)
<223> OTHER INFORMATION: T or R
<220> FEATURE:
<221> NAME/KEY: VARIANT
<222> LOCATION: (16)..(16)
<223> OTHER INFORMATION: A, D, E, G or S
<220> FEATURE:
<221> NAME/KEY: VARIANT
<222> LOCATION: (17)..(17)
<223> OTHER INFORMATION: S or T
<220> FEATURE:
<221> NAME/KEY: MISC_FEATURE
<222> LOCATION: (18)..(18)
<223> OTHER INFORMATION: metabolism inhibiting group or chelator
      attached
<220> FEATURE:
<221> NAME/KEY: VARIANT
<222> LOCATION: (18)..(18)
<223> OTHER INFORMATION: D or E

<400> SEQUENCE: 2

Ser Cys Xaa Cys Xaa Gly Pro Pro Xaa Phe Glu Cys Trp Cys Tyr Xaa
1               5                   10                  15

Xaa Xaa

<210> SEQ ID NO 3
<211> LENGTH: 22
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: metabolism inhibiting group or chelator
      attached
<220> FEATURE:
<221> NAME/KEY: DISULFID
<222> LOCATION: (4)..(16)
<220> FEATURE:
<221> NAME/KEY: VARIANT
<222> LOCATION: (5)..(5)
<223> OTHER INFORMATION: N, H or Y
<220> FEATURE:
<221> NAME/KEY: DISULFID
<222> LOCATION: (6)..(14)
<220> FEATURE:
<221> NAME/KEY: VARIANT
<222> LOCATION: (7)..(7)
<223> OTHER INFORMATION: G, S, T or N
<220> FEATURE:
<221> NAME/KEY: VARIANT
<222> LOCATION: (11)..(11)
<223> OTHER INFORMATION: T or R
<220> FEATURE:
```

```
<221> NAME/KEY: VARIANT
<222> LOCATION: (18)..(18)
<223> OTHER INFORMATION: A, D, E, G or S
<220> FEATURE:
<221> NAME/KEY: VARIANT
<222> LOCATION: (19)..(19)
<223> OTHER INFORMATION: S or T
<220> FEATURE:
<221> NAME/KEY: VARIANT
<222> LOCATION: (20)..(20)
<223> OTHER INFORMATION: D or E
<220> FEATURE:
<221> NAME/KEY: MISC_FEATURE
<222> LOCATION: (22)..(22)
<223> OTHER INFORMATION: metabolism inhibiting group or chelator
      attached

<400> SEQUENCE: 3

Ala Gly Ser Cys Xaa Cys Xaa Gly Pro Pro Xaa Phe Glu Cys Trp Cys
1               5                   10                  15

Tyr Xaa Xaa Xaa Gly Thr
            20

<210> SEQ ID NO 4
<211> LENGTH: 4
<212> TYPE: PRT
<213> ORGANISM: Artificial
<220> FEATURE:
<223> OTHER INFORMATION: synthetic peptide

<400> SEQUENCE: 4

Gly Gly Gly Lys
1

<210> SEQ ID NO 5
<211> LENGTH: 4
<212> TYPE: PRT
<213> ORGANISM: Artificial
<220> FEATURE:
<223> OTHER INFORMATION: synthetic peptide

<400> SEQUENCE: 5

Gly Ser Gly Lys
1

<210> SEQ ID NO 6
<211> LENGTH: 5
<212> TYPE: PRT
<213> ORGANISM: Artificial
<220> FEATURE:
<223> OTHER INFORMATION: synthetic peptide

<400> SEQUENCE: 6

Gly Ser Gly Ser Lys
1               5

<210> SEQ ID NO 7
<211> LENGTH: 26
<212> TYPE: PRT
<213> ORGANISM: Artificial
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: metabolism inhibiting group or chelator
      attached
<220> FEATURE:
<221> NAME/KEY: DISULFID
<222> LOCATION: (4)..(16)
```

```
<220> FEATURE:
<221> NAME/KEY: DISULFID
<222> LOCATION: (6)..(14)
<220> FEATURE:
<221> NAME/KEY: MISC_FEATURE
<222> LOCATION: (26)..(26)
<223> OTHER INFORMATION: metabolism inhibiting group or chelator
      attached

<400> SEQUENCE: 7

Ala Gly Ser Cys Tyr Cys Ser Gly Pro Pro Arg Phe Glu Cys Trp Cys
1               5                   10                  15

Tyr Glu Thr Glu Gly Thr Gly Gly Lys
            20                  25
```